United States Patent [19]
Lübbers

[11] 4,272,485
[45] Jun. 9, 1981

[54] MEMBRANES FOR OPTODES

[75] Inventor: Dietrich W. Lübbers, Dortmund, Fed. Rep. of Germany

[73] Assignee: Max-Planck-Gesellschaft zur Forderung der Wissenschaften e.V., Goettingen, Fed. Rep. of Germany

[21] Appl. No.: 72,781

[22] Filed: Sep. 5, 1979

[30] Foreign Application Priority Data

Dec. 27, 1978 [DE] Fed. Rep. of Germany ....... 2856252

[51] Int. Cl.³ ..................... G01N 21/78; G01N 21/64
[52] U.S. Cl. .................... 422/68; 23/230 B; 356/441; 422/58; 422/50; 435/299
[58] Field of Search ............ 23/232 R, 232 E, 230 B; 422/57, 52, 55, 86, 91, 68, 58, 50; 356/39, 85, 246, 436, 441; 435/299; 204/195 M, 195 P

[56] References Cited

U.S. PATENT DOCUMENTS

| | | | |
|---|---|---|---|
| 3,404,962 | 10/1968 | Medlar et al. | 422/86 |
| 3,572,994 | 3/1971 | Hochstrasser | 23/232 R |
| 3,754,867 | 8/1973 | Guenther | 23/232 R |
| 4,003,707 | 1/1977 | Lubbers et al. | 23/232 R |

*Primary Examiner*—Ronald Serwin
*Attorney, Agent, or Firm*—Michael J. Striker

[57] ABSTRACT

In an indicator chamber (e.g., optode) arrangement including an indicator and a membrane which surrounds it and is impermeable to it, a carrier substance is provided within said membrane for transport of particles to be measured into the indicator chamber. Said carrier is mobile within said membrane. This improvement allows for the preparation of highly selective indicator arrangements and broadens the range of applicability of the method of measurement.

16 Claims, 3 Drawing Figures

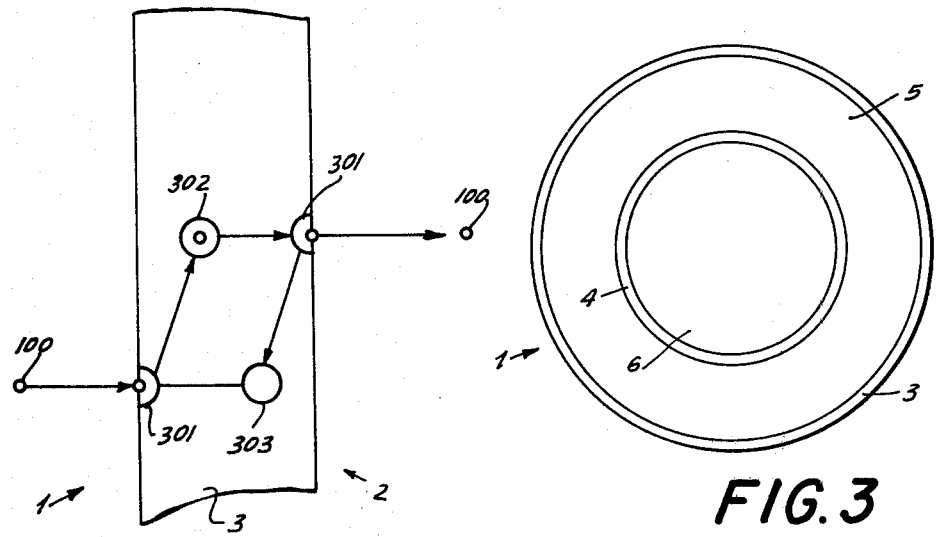
FIG. 1
FIG. 3
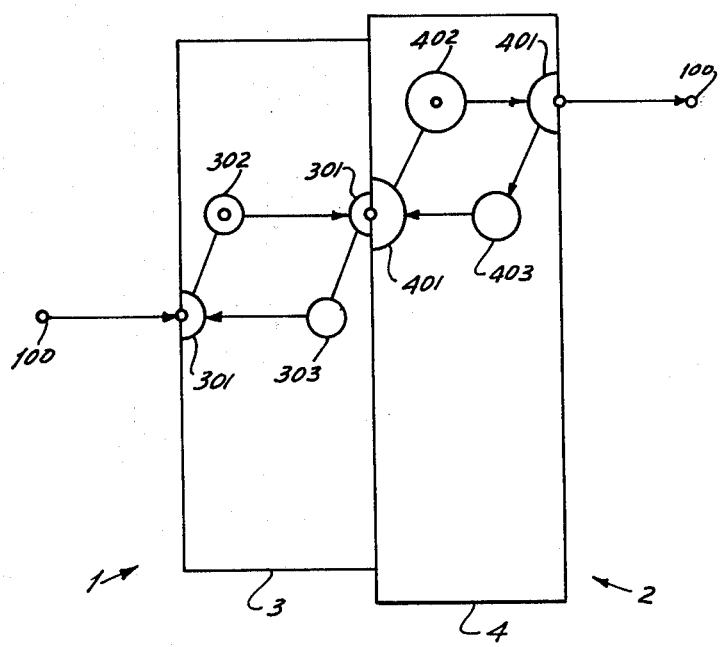
FIG. 2

MEMBRANES FOR OPTODES

BACKGROUND OF THE INVENTION

The invention concerns an indicator chamber (optode) comprising an indicator and a membrane surrounding the indicator and impermeable to it for measurement of concentrations of substance particles by means of e.g. a light measurement system, consisting of a light source, a light receiver and read-out means. In particular, the invention concerns the membrane which surrounds the optode.

The prior art systems operate on the principle that the portion of a composition to be measured is separated from components which disturb the accuracy of measurement. For example, if the oxygen content of blood is to be measured by fluorescence methods, certain protein fractions would render direct readings inaccurate either through their own fluorescence or through binding of the indicator. By separating the measurement area by means of a membrane through which the fraction to be measured may diffuse, blood proteins and other particle fractions are held back, preventing disturbances of the accuracy of measurement.

The disadvantage of the prior art devices lies in the fact that there are only a few types of membranes which exhibit such selective properties; for example, gas/teflon is such a separation pair. The range of applicability of the devices is, therefore, rather restricted. This is in particular unfortunate, in that the method is characterized by a great degree of freedom from side reactions—so that the measurement is not rendered false because of other components—and, in addition, the measurement may be carried out quickly and without special preparation.

SUMMARY OF THE INVENTION

It is, therefore, an object of the invention to provide other separation pairs, i.e., combinations of particles to be measured and of transport membranes, which allow the method to be used in a broad range of possible applications.

This object is achieved through the invention by providing in the membrane mobile carrier substances, by means of which the particles are transported within the membrane.

The advantage of this lies in the fact that there are already known a large number of separation pairs; substances, known as ligands, may be dissolved in solid or liquid membranes and are able to form complexes with the particles to be measured; in most cases, the substances completely surround the particle. Cf., e.g., J. Koryta, Ion-selective Electrodes, Cambridge (1975). It is possible to synthesize such carriers especially designed for a particular type of particle, so that the selectivity can be quite high, while the range of possible applications includes a virtually limitless number of particle types. An example of such a separation pair is the antibiotic valinomycin and $K^+$ ions; the carrier may be dissolved in PVC. See Res. Devel. 25:20-24 (1974); J. Amer. Chem. Soc. 89: 386 (1967).

In principle, the carrier may be either charged or uncharged. If the carrier is electrically charged, then upon take-up of an ion it is transformed into the uncharged state, and thus the membrane becomes neutral as a result of the transport and additional transport energy is not required. If the carrier is electrically neutral, additional transport energy is necessary. The chemical binding, into which a particular carrier type enters with the particle to be transported, should not be so great that the degree of dissociation is too low, as then saturation of the membrane occurs without transport.

If the particle to be transported bonds with the carrier substance, the rate of transport is determined by the degree of dissociation of the particle fraction on both sides of the membrane. In a preferred embodiment of the invention, therefore, a substance is provided within the indicator chamber which binds the particle to be measured. This has the advantage, that on account of the reversible chemical or physical binding, in addition to a minimization of interference with the accuracy of measurement there is also a strengthening of the optical signal for the light measurement system because of a concentration of the particles within the indicator chamber. With respect to the light measurement system, the disclosure of U.S. Pat. No. 4,003,707 is hereby incorporated by reference.

In order to measure particle fractions in aqueous solutions, the membrane and carrier should be lipophilic and simultaneously water-repellent. Conversely, hydrophilic membranes are used to effect a separation in lipid solutions.

Where it is not possible to provide a solid membrane, the carrier may have liquid form and be embedded in a solid matrix of a porosity suitable for the particle fraction. The matrix would thus be sealed with respect to the carrier.

In order to increase the selectivity it is advantageous if more than one membrane with different carriers for transporting the same particle fraction are used one after the other, as the permeability of the total arrangement is more selective than is the case with the single membranes. A particularly simple combination consists of a solid carrier and a liquid carrier employed therewith.

Carrier-containing membranes may also be improved through the use of selective indicators. One may, for example, use the following pairs:

| | | |
|---|---|---|
| Valinomycin | 8-hydroxyquinoline | for $K^+$ |
| Monensin | Zinc uranyl acetate | for $Na^+$ |
| Calcium ionophor* | Calcein, Aequorin | for $Ca^{++}$ |

*Cf. Simon, Biochem. Biophys. Acta 470: 437 (1977).

The selectivity of these fluorescence pairs, together with the selectivity of the carrier used, greatly increases the selectivity of the total system.

It has further been determined, that the selectivity can be improved by providing within the indicator chamber a substance which reacts with the particle, and thereby produces a reaction product which alters the optical properties of the indicator. Through the mediation of a reaction within the indicator chamber, therefore, the presence of a particular type of particle, for which no selective indicator is known, can be determined through a known indicator via a selective intermediate reaction; in effect, the indicator is transformed into one selective for the particle.

Indicator chambers according to the invention may have a flat form, as for the measurement of concentration distributions. They can, however, also be in the form of microcapsules or nanocapsules which may be implanted in liquids or in layers as indicators for use with particle fractions with which they come into contact and through which concentrations may be determined by irradiation and light measurement. They may also be in the form of well-visible macrocapsules implanted near the surface. See generally Speiser, in J. R. Nixon, Marcel Dekker Co., New York (1976), p. 1 ff.

A further use of the invention lies in the measurement of particles which are heavy molecules, i.e., those with higher atomic number. If the carrier is suitable for transport of heavy molecules and instead of light, an electron source is provided, a concentration of the desired particle fraction may be achieved within the indicator chamber through introduction of substances which bind the particles, permitting X-ray analysis in sections. A reaction may also be carried out in vivo in the presence of microcapsules, by which means the reaction product is concentrated or collected within the capsules; subsequent x-ray analysis could then be carried out on sections of tissue. A measurement of heavy molecules in vivo is thereby possible, as the capsules enriched in the heavy molecules could be irradiated by x-ray and the increased shading due to the enrichment densitometrically determined.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 illustrates in schematic form the carrier transport in a single membrane;

FIG. 2 illustratees a double membrane system; and

FIG. 3 illustrates a multiple-layer capsule.

DESCRIPTION OF THE PREFERRED EMBODIMENTS

With reference to FIG. 1, a particle 100 in a solution 1 comes into contact, for example through diffusion, with membrane 3 and a carrier 301 ready to take it up in the membrane. The carrier takes up the particle 100 and the resulting combination 302 diffuses through the membrane 3 to the other side. There the particle 100 is given up to the solvent 2 and the carrier 303, now empty, diffuses back to the first side and is ready to take up another particle on the surface of the membrane. The direction of transport depends solely upon the diffusion parameters, i.e., on the concentration of the particle fraction in solutions 1 and 2.

FIG. 2 illustrates a double membrane system, in which a double membrane 3, 4 surrounds the indicator chamber 2, separating it from solution 1 to be measured. A particle 100 from the concentration to be measured comes into contact with a carrier 301 ready to take up the particle at the membrane surface. The carrier 302 loaded or charged with the particle 100 then comes into contact at the surface of the second membrane 4 with another carrier 401 ready to take up the particle. The carrier-particle combination 402 then travels to the inner border surface of membrane 4 and the particle 100 is introduced into the indicator chamber 2. A reactive substance 201 comes into contact with the particle 100 and thereby is produced the reaction products 203 and 204.

Between membranes 3 and 4 there may also be provided a reaction substance which will react with the type of particle to be measured. In this case, the reaction product may be transported by the carrier in the second membrane. In this way, the selectivity of the entire system may be increased. The same principle may be used any number of times; in particular, in the formation of multi-stage capsules of quite high selectivity.

FIG. 3 illustrates such a capsule. By example, membranes 3 and 4 are provided with carriers. Solution 5 contains a reactive substance; within membrane 4, a selective indicator 6 is provided. The particle to be measured is transported from the composition 1 being measured by means of the carrier of membrane 3 into the reaction chamber 5. The reaction product, for example, is a calcium ion. This is transported into the indicator chamber 6 by means of a calcium-specific carrier in membrane 3. The indicator then permits optical measurement. If a calcium-binding substance is also provided within chamber 6, the concentration of calcium therein is increased, thereby strengthening the measurement signal. For use in biological systems, it is desirable to coat the outside surface of membrane 3 with immunologically neutral substances, in order to minimize rejection or repulsion reactions of the organism.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. In an indicator arrangement comprising an indicator and a membrane forming a chamber surrounding said indicator and impermeable to it, for determination of concentrations of particle components, the improvement comprising providing within said membrane a carrier which is mobile within said membrane and which transports said particles through said membrane.

2. An indicator arrangement as defined in claim 1, wherein said measurement is effected by means of a light measurement system, including a light source, a light receiver and readout means.

3. An indicator arrangement as defined in claim 1, wherein said measurement is effected by means of an x-ray analysis system including an electron source, and said particles are heavy molecules.

4. An indicator arrangement as defined in claim 1, wherein said carrier is electrically charged.

5. An indicator arrangement as defined in claim 1, wherein said carrier is electrically neutral.

6. An indicator arrangement as defined in claim 1, wherein a substance for binding said particles is provided within said chamber formed by said membrane.

7. An indicator arrangement as defined in claim 1, wherein said membrane is lipophilic.

8. An indicator arrangement as defined in claim 1, wherein said membrane is hydrophilic.

9. An indicator arrangement as defined in claim 1, wherein said carrier is in liquid form embedded with a solid matrix of suitable porosity for said particles.

10. An indicator arrangement as defined in claim 1, wherein more than one membrane is employed, said membranes being provided with different carriers for transport of said particles.

11. An indicator arrangement as defined in claim 1, wherein said chamber is in the form of a flat surface.

12. An indicator arrangement as defined in claim 1, wherein said chamber is in the form of a capsule.

13. An indicator arrangement as defined in claim 1, wherein a selective indicator is employed.

14. An indicator arrangement as defined in claim 1, wherein a substance which reacts with said particles is provided within said chamber, said reaction producing reaction products which then modify the optical properties of said indicator.

15. An indicator arrangement as defined in claim 1, wherein a first chamber is provided within a second chamber which surrounds it.

16. An indicator arrangement as defined in claim 15; further comprising additional enveloping membrane chambers.

* * * * *